(12) United States Patent
Julkowski et al.

(10) Patent No.: US 9,415,184 B2
(45) Date of Patent: Aug. 16, 2016

(54) SYSTEM AND METHOD TO OPTIMIZE SLEEP CONDITIONS

(71) Applicant: EDIA LLC, Minneapolis, MN (US)

(72) Inventors: Jeff Julkowski, Naples, FL (US); James Howard, Birmingham, AL (US); Timothy Ziaja, Saint Paul, MN (US)

(73) Assignee: Edia, LLC, Minneapolis, MN (US)

( * ) Notice: Subject to any disclaimer, the term of this patent is extended or adjusted under 35 U.S.C. 154(b) by 94 days.

(21) Appl. No.: 14/170,865

(22) Filed: Feb. 3, 2014

(65) Prior Publication Data

US 2015/0217081 A1 Aug. 6, 2015

(51) Int. Cl.
*A61M 21/02* (2006.01)
*A61M 21/00* (2006.01)

(52) U.S. Cl.
CPC ....... *A61M 21/02* (2013.01); *A61M 2021/0027* (2013.01)

(58) Field of Classification Search
CPC ................ A61M 21/00; A61M 21/02; A61M 2021/0005; A61M 2021/0027; A47G 9/1045; H04R 5/023
See application file for complete search history.

(56) References Cited

U.S. PATENT DOCUMENTS

| 5,713,741 | A | * | 2/1998 | DeMars | A47G 9/1045 434/319 |
| 7,749,155 | B1 | * | 7/2010 | Anderson et al. | 600/28 |
| 2005/0066443 | A1 | * | 3/2005 | Rivera-Wienhold et al. | 5/632 |
| 2007/0275631 | A1 | * | 11/2007 | Tosta | 446/71 |
| 2009/0105524 | A1 | * | 4/2009 | Bressler et al. | 600/27 |

* cited by examiner

*Primary Examiner* — Charles A Marmor, II
*Assistant Examiner* — Carrie R Dorna
(74) *Attorney, Agent, or Firm* — Todd R. Fronek; Larkin Hoffman Daly & Lindgren, Ltd.

(57) ABSTRACT

A system and related method to optimize the process of getting a child to fall asleep. The system is a computer-implemented system comprising a set of functions or algorithms to assist a child develop a routine to fall asleep. The particular routines are dependent on the age of the child, with three categories being toddlers, preschoolers and school-age children. The routines include providing for the generation of a set of sounds for selectable periods of time, dependent on the age group. The sounds include lullabies, stories, songs and white noise. The time periods range from 15-45 minutes. The method involving the use of the sound generation routine establishes a regularity of process that comforts a child and enhances the likelihood of a good transition to sleep.

9 Claims, 3 Drawing Sheets

SYSTEM AND METHOD TO OPTIMIZE SLEEP CONDITIONS

BACKGROUND OF THE INVENTION

1. Field of the Invention

The present invention relates to arrangements to aid people, children in particular, to fall asleep. More particularly, the present invention relates to systems and methods for optimizing the conditions established for people to help them fall asleep.

2. Description of the Prior Art

It is fairly common for children to experience some difficulties going to sleep at bedtime. Infants, toddlers, preschoolers and school-age children have such difficulties from time to time; some more so than others. If a young child has sleep problems, the whole family may be affected, including at bedtime when the focus of attention falls on that child, possibly for an extended period of time, possibly through the night, and the next day when the fallout from a disrupted routine impacts the child and those around the child impacted by the occurrence. There is a need for a system and/or method to improve the circumstances of getting a child to fall to sleep.

If childhood sleep problems are not addressed they can persist into later childhood and teenage years. Lack of good quality sleep in children has been linked to a variety of developmental and behavioral problems. There may be additional aspects of the child's sleep cycle that contribute to, or form a significant part of, such problems not limited to the event of initially falling to sleep. Nevertheless, that first effort at getting the child to fall to sleep can impact the remainder of the sleep cycle. Links have been suggested between sleepiness and increased oppositional and inattentive behavior, impaired verbal fluency and creativity, a reduction in the speed and accuracy at which tasks are completed and a decrease in the ability to perform abstract problem solving. It is therefore clear that addressing childhood sleep problems, which may include ensuring that the sleep cycle begins as effectively as possible, has value for a child. Additionally, a smooth transition from activity to sleep can be of consequential benefit to the rest of the family.

As children age, the types of sleep problems they can suffer from change. Newly born babies of up to around two months are not able to distinguish night from day and typically sleep for numerous short periods. From two months to about two years of age, children start to sleep for longer periods and have to learn to adjust their sleep patterns in order to sleep during the night and be active during the day. A child learns how to sleep and does so as a function of the environment. Among other things, such as room noise or temperature, for example, if the child associates the onset of sleep with receiving attention from a particular parent, for example, it may be necessary to have that parent in attendance at sleep time. As the time frame for falling to sleep expands, the reliance on that parent's attendance becomes more necessary. It can become difficult to get the child to fall asleep under any other conditions. The child may cry until that particular condition exists. The need for the existence of that specific condition can be disruptive for all concerned, particularly as the time involved increases.

As children become more independent from about to two to five years old, they often start to stall at bedtime, refuse to go to bed or leave their bedroom. This can be because the children seek attention from a parent, parents or other caregiver, and may prioritize the need for that association over giving in to the feeling tiredness. If the caregiver does not enforce conditions that provide regularity to the sleep cycle, older children learn that they can get away with staying up later if they are disruptive to the process at bedtime. This often leads to the children not receiving the duration of sleep they require. These problems can be aggravated further by busy sleeping environments, such as a room shared with another child or sleep-incompatible behaviors such as late-night television watching. Once a child has developed inappropriate sleep habits they can be difficult for a caregiver to fix. At least one study has suggested that children ages 2-12 fall asleep in about 17-19 minutes. That may be quite a long time for the child to miss out on sleep and the caregiver to spend in an effort, directly or indirectly, to get a child to sleep.

For school age children of five years and above, the imposition of a different weekday and weekend schedule can lead to sleeping difficulties, including the ability to get up early in the morning and going to bed earlier at night in order to be able to get up early in the morning. Furthermore, any sort of stimulating activity, including television in the bedroom and rigorous physical activity just before bedtime, for example, can lead to a delay in the onset of sleep and accompanying problems with daytime sleepiness. If unaddressed these problems can have a deleterious effect on the performance of the child at school and in later life.

Fortunately, many sleep problems in children can be addressed by established behavioral means. By setting and enforcing appropriate sleep times, removing distractions, ensuring a good sleep environment and timing parental contact, the child's quality of sleep can be optimized. The difficulty arises in establishing those conditions to ensure such a good overall environment to facilitate the onset of sleep. It is believed, and is the premise of the present invention, that this optimization is most likely to occur when the child develops his or her own sleep skill. That is, the child will develop the best sleep cycle when he or she makes the effect transition from when the caregiver departs the child's presence to when sleep begins. That transition is dependent on the child's developmental stage but it can be generally characterized with respect to toddlers, preschoolers and your schoolchildren. What is needed is a system and related method to optimize that transition period. Currently, while there are skill building products, specifically periodicals and work books that help build children's skills in mathematics, reading and writing, there are no skill building products in the marketplace that help build effective sleep skills in children.

SUMMARY OF THE INVENTION

It is an object of the present invention to provide a system and related method to enhance the likelihood that a child will fall to sleep within a desired period of time after going to bed and with minimal caregiver intervention. The system and related method should be natural and not the subject of pharmaceutical assistance. Further, the system and method should provide for that sleep initiation optimization in a way that helps, or at least does not impact negatively, the child's opportunity to get an effective amount of sleep. Moreover, it is an object of the present invention to carry over to any sleep or relaxed circumstance, such as a nap, the routine or routines provided hereunder as a way to reinforce the sleep transition activity most effective at ensuring sleep will take place as efficiently as possible.

These and other objects are achieved with the present invention, which provides a system and related method to optimize the conditions for getting a child to fall to sleep. The system and method include an algorithm that may comprise a subset of algorithms, wherein each sub-algorithm is established as a function of a child's age, to be selected and followed to achieve the desired goal. Each algorithm defines a series of steps to be carried out in the course of getting the child to go to sleep. The steps may be varied in form and order and additional steps may be employed as a function of the particular child and particular goals. The system includes particular conditions described as follows.

Based on physician and sleep expert data, the present invention comprises three primary sub-algorithms, one for each of the age ranges of toddlers, preschoolers and school-age children. It is to be understood that further sub-algorithms may be established for other age groups or narrower age ranges as a function of the determined specific optimal conditions for that group or range to fall to sleep. The sub-algorithms include particular steps to carry out, each of which ends with a sound routine such as is indicated in Table 1. It is to be understood that the specific times and activities disclosed in Table 1 are exemplary and are not intended to limit the scope of the invention. For purposes of the present invention "elo time" means the transition period when parents leave the nighttime routine and the child develops his or her own sleep skill. In particular, elo time may include the use of an instrumentality, such as a pillow available from EDIA, LLC, and later described herein, which is configured to sense contact and generate sound, for example, designed to encourage the child to maintain his or her head on the pillow. The activities or events carried out during elo time include the opening chime, lullabies/songs, stories and sounds listed in Table 1. An instrument such as the sleep pillow is described in pending U.S. patent application Ser. No. 13/941,396 entitled "Sleep Assistance Article and Related Methods of Use." That application is owned by a common assignee and its content is incorporated herein by reference. The volume, tone and cadence of the particular sleep sounds routine within a particular age-specific algorithm begins with a recognizable chime, and slowly diminishes in tone, pace and volume until a sound such as white noise at the close of the routine puts the child to sleep.

TABLE 1

| Age | Elo time | Opening chime | Lullabies/ song | Stories | Sounds |
| --- | --- | --- | --- | --- | --- |
| 1-3 | 15-20 mins | 15 secs | 3-5 mins | 10 mins | 2-3 mins |
| 3-6 | 20-30 mins | 5 secs | 3-5 mins | 15-20 mins | 2-3 mins |
| 6-10 | 30-45 | 5 secs | 0 | 30-45 | 2-3 mins |

The instrument, such as the pillow, may be programmed to include pre-loaded sounds. It may be accessible wirelessly or by wire to means for adding and/or changing audible content. It may also be connected to, such as by wireless communication, or associated with, other devices that may be useful in the effort to assist a child in falling to sleep. For example, the instrument may be associated with a nightlight. The nightlight may remain on during elo time and programmed to shut off at the end of that time or at such other time as desired. Each may be separately or jointly activated. For example, actuation of a switch on the pillow may activate the pillow and the nightlight.

Data have shown that the overall bedtime routine varies by age, child and parent, however the overall time should not exceed one hour, with the last 20% of that timeframe being elo time. The last 15-20 minutes of the nighttime routine are the most stressful and the most important to a parent shaping and a child learning how to build their sleep skills. In order for the skill of sleep to be developed, parents must continually reinforce these shaped behaviors in other segments of sleep such as napping, calming, quiet time, time outs, driving, strollers and travel. If you as a parent are the only consistent component to a good routine or a bad routine, your child is not developing his or her own sleep skills. Training or teaching is something parents do, learning is what children do.

The particular algorithm groupings are established as follows, with a brief description of the sleep activities of children in these age ranges.

1-3 Years Old: 12-14 Hours of Sleep Per Day
   Average time for routine: 1 hour
   Begin at 7:00 pm-Asleep by 8:00 pm-8:00 am/10:00 am
   elo time: 15 mins As your child moves past the first year toward 18-21 months of age he will likely lose his morning nap and nap only once a day. While toddlers need up to 14 hours a day of sleep, they typically get only about 10. Most children from about 21 to 36 months of age still need one nap a day, which may range from one to three and a half hours long. They typically go to bed between 7 and 9 p.m. and wake up between 6 and 8 a.m.

3-6 Years Old: 10-12 Hours of Sleep Per Day
   Average time for routine: 1 hour
   Begin at 7:00 pm-Asleep by 8:00 pm-6:00/8:00 am
   elo time: 20-30 mins Children at this age typically go to bed between 7 and 9 p.m. and wake up around 6 and 8 a.m., just as they did when they were younger. At 3, most children are still napping, while at 5, most are not. Naps gradually become shorter as well. New sleep problems do not usually develop after 3 years of age.

6-10 Years Old: 10-11 Hours of Sleep Per Day
   Average time for routine: 45 minutes
   Begin at 8:00 pm-Asleep by 9:00 pm-7:00 am
   elo time: 30-45

At these ages, with social, school, and family activities, bedtimes gradually become later and later, with most 12-years-olds going to bed at about 9 p.m. There is still a wide range of bedtimes, from 7:30 to 10 p.m., as well as total sleep times, from 9 to 12 hours, although the average is only about 9 hours.

The present invention provides four primary auditory segments during the elo time. Elo time may begin when the child gets in bed or prior to that. The first is an initial introductory sound that signals to the child that the routine is about to begin. The remaining three segments include three types of audible educational content, which includes a collection of timed audible content found in stories, lullabies and sounds. The routine provides for a mix of these audible elements that begin, after the sound introduction, one or more stories, one or more lullabies and then a tapering off to a library of sounds or white noise. The cadence of sound, stories, songs and diminished tone provide the calming experience required to help a child learn to self sooth and to develop their own positive sleep habits. The sounds may be generated by any sort of device including, for example, the sleep skill building pillow described by EDIA, LLC, noted above, which includes a library of audible educational content to help parents teach and children learn the life skill of sleep. The Edia pillow may be controlled to regulate sound initiation and stoppage and sound selection, including providing for customized sounds to be generated with the timing for different sounds as indicated herein.

The system and related method of the present invention provide an advantage in helping a child fall to sleep. While this description of the invention has centered on aiding a child to develop skills effective to enable self control of falling asleep, it may also be useful for some who is not a child. The generation of sounds, possibly associated with other stimuli, such as a nightlight, of a certain type for a certain period of time for each sound type aids the person to get into a routine that optimizes the process of falling asleep. This and other advantages of the invention will become more apparent upon review of the following detailed description, the accompanying drawings and the appended claims.

DETAILED DESCRIPTION OF THE PREFERRED EMBODIMENTS OF THE INVENTION

Figure 1:
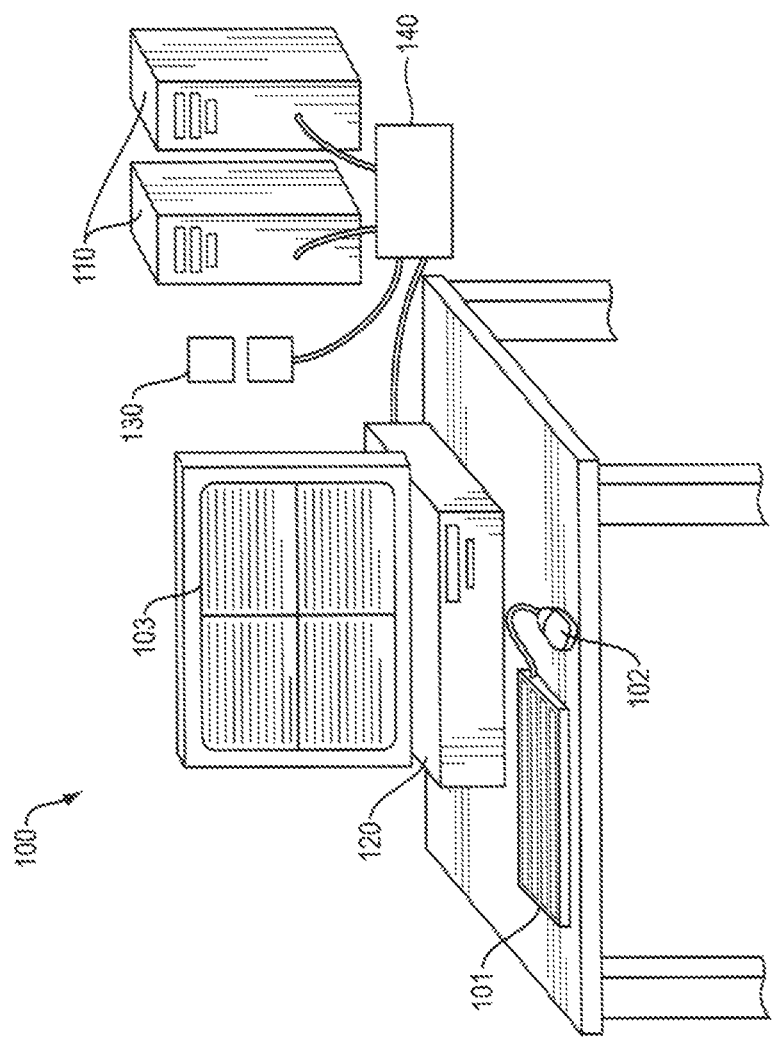
FIG. 1 is a simplified representation of a computing system suitable for carrying out the steps of the method of the present invention as described herein.

The present invention is a system and method for optimizing sleep conditions, particularly for a child. The system and method and are embodied in a computing system programmed to perform functional steps associated with the storing of the information for the purpose of accessing it and carrying out instructions based on that information. Any type of computing system suitable to store information in the amount of interest and to generate and/or initiate instructions of interest on the information may be employed and is represented generally in FIG. 1. The computer system 100 shown is only one example of a suitable computing environment and is not intended to suggest any limitation as to the scope of use or functionality of the invention. For example, the computer system 100 may be associated with local or remote computing means, such as one or more central computers, such as server 110 in a local area network, a metropolitan area network, a wide area network, or through intranet and internet connections.

The computer system 100 may include one or more discrete computer processor devices, represented by desktop computer 120, for example. Examples of well known computing devices that may be suitable for use with the invention include, but are not limited to, personal computers, server computers, hand-held or laptop devices, tablet computers, multiprocessor systems, microprocessor-based systems, set top boxes, programmable consumer electronics, network PCs, minicomputers, mainframe computers, distributed computing environments that include any of the above systems or devices, and the like. The computer system 100 may include computer devices operated by one or more users, such as through a desktop, laptop, or servers, and/or one or more providers of services corresponding to one or more functions of the invention.

The server 110, the computer processor 120, or a combination of both may be programmed to include one or more of the functions of the invention system. A database of the present invention for gathering, storing and making accessible the process, sounds and/or sound programming information, is represented by Database 130. For the purpose of the description of the present invention, a database is a collection of stored data that are logically related. Although there are different types of databases, and the Database 130 of the present invention may be any of such types, it is preferably a database with a database management system, comprising tables made up of rows and columns. Data stored in the tables are accessed or updated using database queries submitted to the database system.

Database 130 may be associated with the server 110, the computer processor 120, other computing devices, or any combination thereof, and includes information related to the use of the system of the present invention. The Database 130 may be associated with a single computing device or a plurality of devices. The Database 130 may be centrally located or it may be distributed locally or widely. The Database 130 is populated and updated with information associated with the timing, type and form of sounds and may also be used to store information associated with a child's sleep routine. All of the devices may be interconnected through one or more signal exchange devices, such as router/switch 140.

The invention may be described in the general context of computer-executable instructions, such as program modules, being executed by a computer such as the computer system 100. Generally, program modules include routines, programs, objects, components, data structures, etc. that perform particular tasks or implement particular abstract data types. As indicated above, the system of the present invention may also be practiced in distributed computing environments where tasks are performed by remote processing devices that are linked through a communications network or other data transmission medium. In a distributed computing environment, program function modules and other data may be located in both local and remote computer storage media including memory storage devices.

The computer processor 120 and interactive drives, memory storage devices, databases, including but not limited to the Database 130, and peripherals may be interconnected through one or more computer system buses. The system buses may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

The computer system 100 typically includes a variety of computer readable media. Computer readable media can be any available media that can be accessed by computer system 100 and includes both volatile and non-volatile media, removable and non-removable media. By way of example, and not limitation, computer readable media may comprise computer storage media and communication media. Computer storage media include volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by the computer system 100.

The computer system 100 further includes computer storage media in the form of volatile and/or non-volatile memory such as Read Only Memory (ROM) and Random Access memory (RAM). RAM typically contains data and/or program modules that are accessible to and/or operated on by computer processor 120. That is, RAM may include application programs, such as the functional modules of the system of the present invention, and information in the form of data. The computer system 100 may also include other removable/non-removable, volatile/non-volatile computer storage and access media. For example, the computer system 100 may include a hard disk drive to read from and/or write to non-removable, non-volatile magnetic media, a magnetic disk drive to read to and/or write from a removable, non-volatile magnetic disk, and an optical disk drive to read to and/or write from a removable, non-volatile optical disk, such as a CD-ROM or other optical media. Other removable/non-removable, volatile/non-volatile computer storage media that can be used in the computer system 100 to perform the functional steps associated with the system and method of the present invention include, but are not limited to, magnetic tape cassettes, flash memory cards, digital versatile disks, digital video tape, solid state RAM, solid state ROM, and the like.

The drives and their associated computer storage media described above provide storage of computer readable instructions, data structures, program modules and other data for the computer processor 120. A user may enter commands and information into the computer processor 120 through input devices such as a keyboard 101 and a pointing device 102, commonly referred to as a mouse, trackball or touch pad. Other input devices (not shown) may include a microphone, joystick, game pad, satellite dish, scanner, or the like. These and other input devices are connected to the computer processor 120 through the system bus, or other bus structures, such as a parallel port, game port or a universal serial bus (USB), but is not limited thereto. A monitor 103 or other type of display device is also connected to the computer processor 120 through the system bus or other bus arrangement. In addition to the monitor 103, the computer processor 120 may be connected to other peripheral output devices, such as printers (not shown). Commands and information may be entered by one or more users any one or more of whom may be located in the same or different locations. Commands and information may be entered at designated or random times.

The computer processor 120 may be configured and arranged to perform functions and steps embodied in computer instructions stored and accessed in any one or more of the manners described. The functions and steps, such as the functions and steps of the implementation of the sub-algorithms of the present invention, individually or in combination, may be implemented as a computer program product tangibly as computer-readable signals on a computer-readable medium, such as any one or more of the computer-readable media described. Such computer program product may include computer-readable signals tangibly embodied on the computer-readable medium, where such signals define instructions, for example, as part of one or more programs that, as a result of being executed by the computer processor 120, instruct the computer processor 120 to perform one or more processes or acts described herein, and/or various examples, variations and combinations thereof. Such instructions may be written in any of a plurality of programming languages, for example, XML, JAVA, C++, or any other language suitable for the purpose of the present invention, or any of a variety of combinations thereof. Information entry may be effected using such programming languages as well as other applications including for example and in no way limited thereto, database programs ACCESS and DB2. The computer-readable medium on which such instructions are stored may reside on one or more of the components described above and may be distributed across one or more such components.

Figure 2:
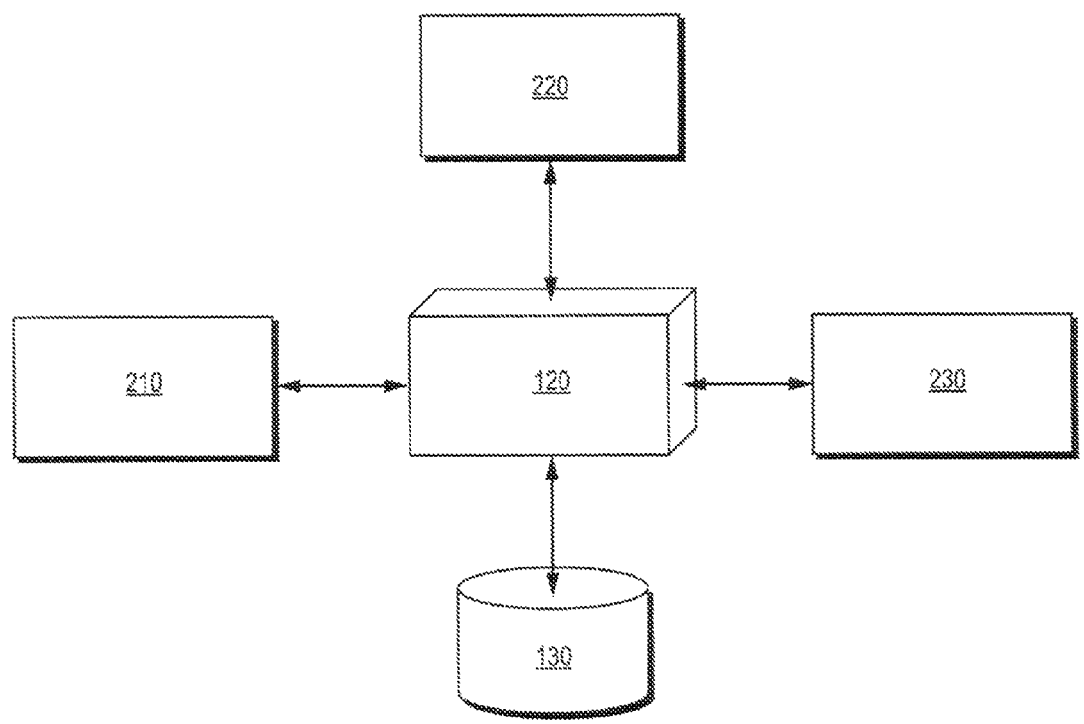
FIG. 2 is a simplified flow diagram representing primary functions of the system of the present invention.

With reference to FIG. 2, a sleep optimization system 200 of the present invention includes a plurality of functions embodied in one or more computer programs executable through the computer processor 120 of the computer system 100, wherein non-transitory signals are exchanged between the functions and the computer processor 120, and between the database 130 and the functions through the computer processor 120. Primary functions of the system 200 include a toddler routine function 210, a preschooler routine function 220 and a school-age routine function 230, each representing primary sub-algorithms. All or a portion of the identified functions may be employed in carrying out steps of three associated sub-algorithms that establish effective routines for getting a child to establish good sleep initiation skills. Other such routine functions may be established for other age groups and/or ranges. The toddler routine function 210 is arranged to generate a set of sounds within a selectable time period for each sound of the sound set suitable for easing a toddler to sleep in accordance with the example form represented in Table 1. The preschooler routine function 220 is arranged to generate a set of sounds within a selectable time period for each sound of the sound set suitable for easing a preschooler to sleep in accordance with the example form represented in Table 1. The school-age routine function 230 is arranged to generate a set of sounds within a selectable time period for each sound of the sound set suitable for easing a school-age child to sleep in accordance with the example form represented in Table 1.

The system 200 provides for storage of information in the database 130, including particular songs, lullabies, stories and white noise options. It may also include customized sounds including, for example, stories and/or sounds read or sung by a caregiver such as a parent whose voice is familiar to the child. The system 200 further provides for the storage of information of interest in carrying out the steps of the algorithms described. For example, the sleep activities of a child before and after carrying out the routines or with variations in the steps carried out or the content of particular steps. Each of the functions 210-230 may be contained as part of the computer system 200, with access to viewing them and, possibly, varying them through the display and interface of the computer system 100. Association with other devices and interconnectivity therewith, such as a nightlight, for example, may be included as part of the programming.

A toddler can understand and appreciate the consistency and predictability of a regular sleep initiation routine and feel more relaxed about sleep when carrying out that routine. The more relaxed he is, the more likely he'll go to bed easily and fall asleep quickly. Stick to your routine as best you can even when you're not home—it can make it easier for your toddler to settle down in unfamiliar surroundings. The specifics of the routine may be customized. There is the standard bath, putting on pajamas, reading a story and having a cuddle or you can play a quiet game. Just make sure you choose something that helps calm your toddler, not gear him up. The routine may begin in the bathroom or the living room, but it should end in the toddler's bedroom. It is important to teach the toddler that his room is a nice place to be, not just where he is "banished" at bedtime. If he gets upset as he sees you walk out the door after you tuck him in, you may tell him you will be back to check on him in a few minutes. In all likelihood, he'll be fast asleep by the time you return.

Figure 3:
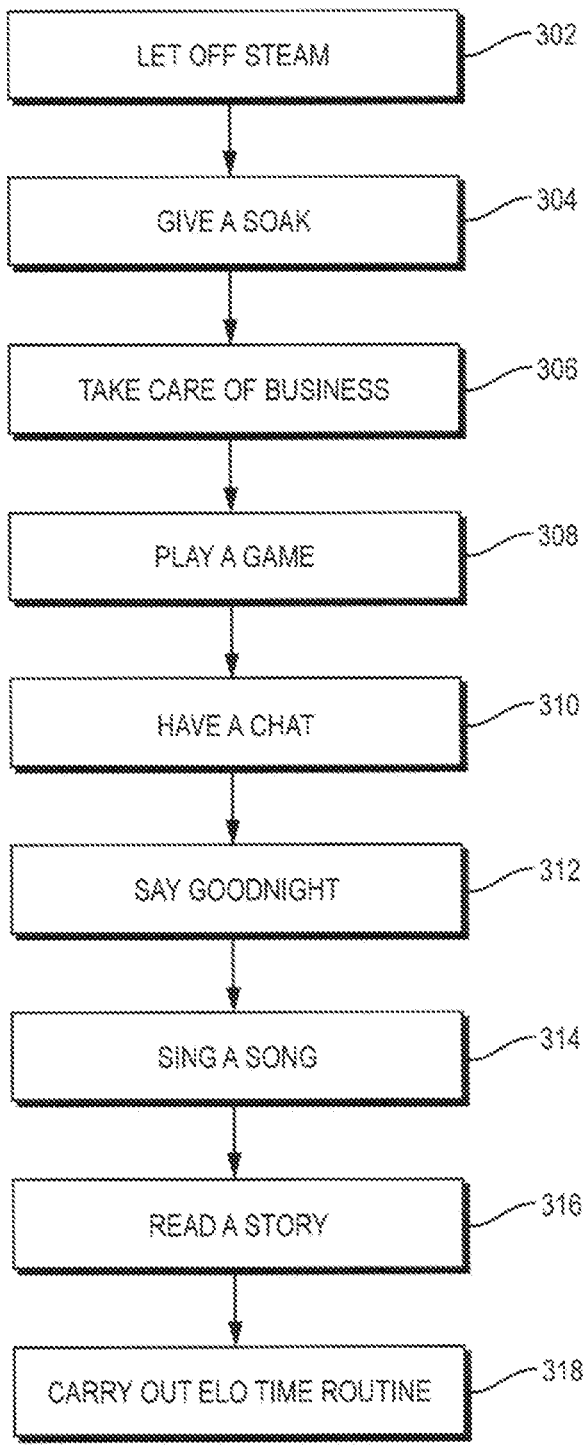
FIG. 3 is flow diagram showing primary steps of a method of the present invention for toddlers, including the elo time component of the method.

With reference to FIG. 3, a method 300 using function 210 of the system 200 is provided to get a toddler to sleep. The method 300 includes optional step 302 of letting the child blow off steam. Sometimes it helps to let the toddler get any pent-up energy out of his system before trying to settle him down for the night. As long as you follow up any rowdy play with something calmer and quieter—like a bath and bedtime story—before he goes to sleep, it can be the first step toward bedtime. Next, optional step 304 involves giving the toddler a bath. One of the most popular parts of many bedtime rituals is a bath. Sitting in warm water is a soothing experience and getting the toddler warm, clean and dry is a great way to ease him into bedtime. A bath is also a wonderful way for a caregiver to spend some special time with the toddler. If the toddler gets excited during baths or does not enjoy them, it is probably better to leave them out of the night-time ritual. Instead, skip this step and proceed with one or more of the other steps prior to elo time. Next, step 306 may be carried out. The toddler's getting-ready-for-bed routine can include washing his face and hands, brushing his teeth, a nappy change or trip to the potty (if he's old enough), and getting into his pajamas. It is important to start the habit of teeth brushing at a young age so your toddler gets used to it. After that, optional step 308 may be used to calm the toddler. Playing a quiet game in the living room or on the floor of the toddler's bedroom is a great way to spend some fun time with him before bed. Older toddlers may enjoy simple puzzles or card games, and younger ones are always entertained by peek-a-boo. Your game can be as simple as taking turns saying the alphabet or counting to 10. Whatever entertains your toddler without getting him overly excited is fine. Before he gets into bed, hide something there for him to find—a toy, a postcard or an interesting object—and then talk about it together. Just be sure to remove the object before you leave.

With continuing reference to FIG. 3, step 310 may be used as part of the routine. Bedtime is a nice chance for toddlers and their parents to spend some time talking to each other. Discuss your daily routine and ask your child to tell you about the best and worst things that happened to him, as well as anything that is worrying him. This may help him work through any anxieties or fears he's harboring and let him get a better night's sleep. Of course, you do not have to wait until your toddler can give you a detailed narrative of the day's events. Review his day for him until he's really able to contribute. Next, step 312 involves more than just saying goodnight. Many toddlers enjoy going around the room or the house and saying goodnight to favorite toys, people and other objects. Know when to say when, though: if your toddler insists on saying goodnight to every single stuffed toy in his bedroom, it is a safe bet he is trying to put off bedtime a little longer. Once that has been accomplished, step 314 involves singing a lullaby or using a device such as the EDIA pillow to generate a lullaby sound, as referenced in Table 1. Additionally or alternatively, step 316 provides for reading a bedtime story. Not only will your toddler learn new words—studies have shown that language skills and even intelligence can depend on a child's daily exposure to a large vocabulary—but he will also benefit from time spent with you. Finally, or in place of the bedtime story reading, and in particular for older children, a device such as the EDIA pillow may be used as part of step 318 to generate sounds of the type described in Table 1 for the time periods suggested in Table 1.

The present invention has been described with respect to a particular embodiment or embodiments. Nevertheless, it is to be understood that various modifications may be made without departing from the spirit and scope of the invention. All equivalents are deemed to fall within the scope of this description of the invention as provided in the following claims.

What is claimed is:

1. A computer-implemented system used to optimize sleep initiation for a child having an age of one of a toddler, a preschooler and school-age, comprising:
    a computer storing a database populated with information associated with timing, type and form of steps for a child sleep routine for a selected timeframe that includes an elo time period defining a plurality of functions;
    a signal exchange device connectable with the computer;
    a first computing device separate from the computer and connectable with the computer through the signal exchange device and having a first computer processor configured to perform one or more steps during the selected timeframe and associated with the child sleep routine stored in the database prior to the elo time period;
    a second computing device separate from the computer and the first computing device, positioned within a pillow and connectable to the first computer processor through the signal exchange device, comprising:
        a contact sensor configured to sense contact with the pillow;
        a speaker positioned within the pillow and configured to generate sound; and
    a second computer processor positioned within the pillow and electrically coupled with the contact sensor and the speaker, wherein upon the contact sensor sensing contact with the pillow, the second computer processor initiates programming to perform, as a function of the age of the child and based on the child sleep routine, one of the plurality of functions stored in the database during the elo time, the plurality of functions comprising:
        a) a toddler routine function arranged to generate a set of sounds using the speaker within the elo time period for each sound of the sound set suitable for easing a toddler to sleep;
        b) a preschooler routine function arranged to generate a set of sounds using the speaker within the elo time period for each sound of the sound set suitable for easing a preschooler to sleep; and
        c) a school-age routine function arranged to generate a set of sounds using the speaker within the elo time period for each sound of the sound set suitable for easing a school-age child to sleep.

2. The computer-implemented system of claim 1 wherein the set of sounds includes lullabies, stories and white noise.

3. The computer-implemented system of claim 2 wherein the set of sounds further includes an initialization chime.

4. The computer-implemented system of claim 1 wherein the elo time for the toddler routine function is 15-20 minutes, for the preschooler routing function is 20-30 minutes and for the school-age routine function is 30-45 minutes.

5. A method to optimize sleep initiation for a toddler comprising the steps of:
    a) using a computer, a first computing device separate from the computer and a second computing device separate from the computer, each of the first computing device and the second computing device connectable through a signal exchange device to facilitate a child sleep routine for a selected timeframe that includes an elo time period,
    b) during the selected timeframe and prior to the elo time period, performing one or more steps using the first computing device and the toddler to provide a determination of whether an elo time routine should be initiated for the toddler; and
    c) carrying out an elo time routine using the second computing device, wherein the elo time routine includes sensing contact of the toddler with a pillow using a contact sensor associated with the pillow and, in response to sensing contact of the toddler with the pillow, generating a series of sounds using a speaker associated with the second computing device during the elo time period while the toddler maintains contact with the pillow.

6. The method of claim 5 wherein the set of sounds includes lullabies, stories and white noise.

7. The method of claim 6 wherein the set of sounds further includes an initialization chime.

8. The method of claim 5 wherein the selectable period of time is 15-20 minutes.

9. The method of claim 5 further comprising the step of giving the toddler a bath prior to carrying out the elo time routine.

* * * * *